US00PP10922P

United States Patent [19]

Wain

[11] Patent Number: Plant 10,922

[45] Date of Patent: May 25, 1999

[54] CHRYSANTHEMUM PLANT NAMED 'LEMON LADY'

[75] Inventor: Peter Wain, Hapshire, United Kingdom

[73] Assignee: Cleangro, Ltd., West Sussex, United Kingdom

[21] Appl. No.: 08/936,966

[22] Filed: Sep. 25, 1997

[51] Int. Cl.[6] ..... A01H 5/00

[52] U.S. Cl. ..... Plt./289

[58] Field of Search ..... Plt./78, 289

[56] References Cited

U.S. PATENT DOCUMENTS

P.P. 8,573 2/1994 Wain ..... Plt./80

*Primary Examiner*—Howard J. Locker

*Attorney, Agent, or Firm*—Christie, Parker & Hale, LLP

[57] ABSTRACT

A new plant variety of pot forcing Chrysanthemum producing yellow flowers.

1 Drawing Sheet

BACKGROUND OF THE INVENTION

The present invention is directed to a new and distinct variety of Chrysanthemum botanically classified as *Dendranthema grandiflora*. The varietal denomination of the new Chrysanthemum is 'Lemon Lady'.

The new variety is a natural sport discovered as one branch on a plant in a commercial greenhouse planting of the variety Wain's 'Pink Lady' (U.S. Plant Pat. No. 8,573) in Nipomo, Calif. The new variety has been asexually reproduced by vegetative cuttings in Ventura County, Calif. and the distinguishing characteristics are retained through successive generations of asexual reproduction.

SUMMARY OF THE INVENTION

'Lemon Lady' is a pot forcing Chrysanthemum plant variety producing large flowers with yellow ray florets and strong sturdy stems.

COMPARISON WITH PARENT

The new variety differs from its parent in ray floret color. 'Lemon Lady' is a slightly shorter plant when given the same cultural treatments as its parent with an average height of about 25 cm, whereas the average height of Wain's 'Pink Lady' is about 29 cm.

In day temperature above about 75° F. the ray flowers of Wain's 'Pink Lady' will fade in color slightly while 'Lemon Lady' shows little or no fading. The flower diameter of 'Lemon Lady' averages about 9 cm compared to an average of about 7.7 cm for Wain's 'Pink Lady'.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of October. 'Lemon Lady' has not been observed under all possible environmental conditions. The phenotype may vary with variations in the environment such as temperature, light intensity, day length and cultural conditions. In the following description color is described by reference to The Royal Horticultural Society Colour Chart.

Plants of the new variety have been grown successfully under temperature conditions averaging about 65° F. at night and about 75–80° F. during the day under light conditions of about 5,000–6,000 foot candles. The plants respond well to use of growth retardant, such as one B9 treatment at about 2000 ppm. To produce a commecial product the plants may be pinched once and center bud removed. It has been observed that the shelf life of 'Lemon Lady' is about 18 days with the response time of about 9 weeks.

Plant

Habit: Upright.
Height: About 25 cm after application of growth retardant as described.
Branching characteristics: Fair.
Number of brakes from pinch: About 3 per pinch.
Typical container size to be grown in: 4", 5", 6", 8", 10".
Length of lateral branches: Average — about 18.5 cm.
Stem color: Near 143C.

Foliage

Leaf arrangement: Alternate.
Leaves on lateral branch: Not very leafy.
(1) *Size.*—Length — Average about 6.4 cm. Width — Average about 4.3 cm.
(2) *Shape.*—Ovate.
(3) *Attachment.*—Petioled (almost sessile).
(4) *Apex.*—Some acute, some obtuse.
(4) *Base.*—Tapered.

| | | | |
|---|---|---|---|
| (6) | Color: | Mature | Young |
| | Top: | Near 147A | Near 147A |
| | Bottom: | Near 138B | Near 138B |

Margin: Lobed, serrate (slight).
Aspect: Flat, curving under with age.
Surface characteristics:
*Top.*—Puberulent.
*Bottom.*—Puberulent.
Petiole:
(1) *Length.*—About 0.8 cm.
(2) *Color.*—Near 143C.
(3) *Other characteristics.*—Very stiff.
Stipule: 2 per mature leaf, 2 or 3 lobed.

Flower

Inflorescence form: Cymose cluster.
Flower form: Decorative.
Flower shape: Slightly irregular circle.
Flower color (general): Clear lemon yellow.
Blooms: About 3 blooms per branch average.
(1) *Diameter.*—Average about 9 cm.
(2) *Depth.*—Average about 1.5 cm.
(3) *Longevity on plant.*—About 18 day shelf life.
Sepal:
(1) *Number.*—About 24 average.
(2) *Color.*—Near 137C.
(3) *General appearance.*—Somewhat membranous.
Peduncle:
(1) *Length.*—Average about 6 cm.
(2) *Habit.*—Upright.
(3) *Surface.*—Tomentose.
(4) *Color.*—Near 137C.
(5) *Strength.*—Brittle.
Bud:
(1) *Shape.*—Flattened sphere.
(2) *Diameter.*—Avg. about 0.8 cm.
(3) *Color.*—Near 144A.
(4) *Height.*—About 0.5 cm.
Ray florets:
(1) *Number per flower.*—Average about 220.
(2) *Fused.*—No.
(3) *Texture.*—Slight sheen.
(4) *Shape.*—Elliptic.
(5) *Apex.*—3-lobed.
(6) *Base.*—Tapered.
(7) *Margin.*—Entire.
(8) *Aspect.*—Curls inward.
(9) *Length.*—Avg. about 4 cm.
(10) *Width.*—Avg. about 1.3 cm.
*Color — top side.*—Immature: Near 4C. Mature: Near 9D. Fading: Near 4D.
*Color — under side.*—Immature: Near 4 C. Mature: Near 5D. Fading: Near 2D.
Disc florets:
(1) *Number per flower.*—About 22 average.
(2) *Texture.*—Shiny.
(3) *Shape.*—Cylindric.
(4) *Margin.*—Entire.
(5) *Length.*—About 0.3 cm.
(6) *Width.*—About 0.9 cm.
*Color.*—Immature: Near 16B. Mature: Near 16A, white base. Fading: Near 23B.
*Fragrance.*—Fragrance of entire bloom is faint, musty floral fragrance.
Description of flower as it ages: Center stays tight, outer ray florets loose but stay flat, do not drop down to make a sphere. Flower color lightens, ray florets drop off before flower is spent.

Reproductive Organs

Ray florets:
*Pistillate.*—(1) Pistil number: 1 per floret. (2) Ovary shape: Domed sphere. (3) Stigma shape: 2 or 3 forked, curved out slightly. (4) Stigma color: Near 7A. (5) Style length: Average about 0.5 cm. (6) Style color: Near 154C.
Disc florets: Staminate and pistillate.
*Pistillate.*—(1) Pistil number: 1 per floret. (2) Stigma shape: linear, near 7A. (3) Style length: About 0.2 cm, clear.
*Staminate.*—(1) Stamen number: About 6. (2) Anther length: About 0.1 cm. (3) Anther shape: linear, near 13A. (4) Pollen color: Near 23A. (5) Pollen quantity: Abundant.

What is claimed is:

1. A new and distinct Chrysanthemum plant of the variety substantially as herein shown and described.

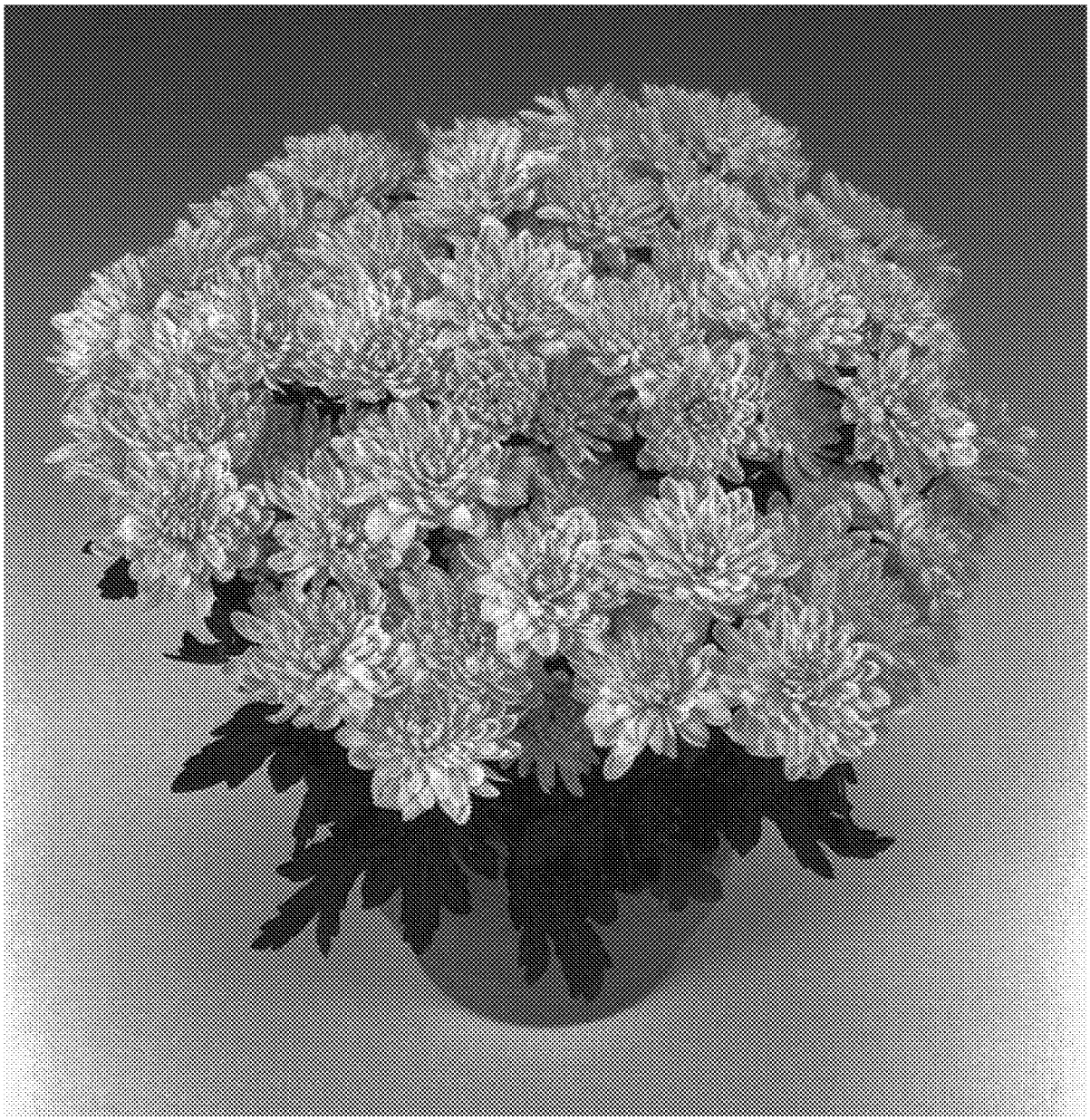

* * * * *